(12) United States Patent
Shinmura et al.

(10) Patent No.: US 7,122,032 B2
(45) Date of Patent: Oct. 17, 2006

(54) OPERATION SYSTEM AND MOUNTING DEVICE FOR EXTERNAL DEVICE FOR USE IN THE OPERATION SYSTEM

(75) Inventors: Toru Shinmura, Hachioji (JP); Gakuji Higuchi, Ina (JP); Tomoaki Yamashita, Hachioji (JP); Kenji Omachi, Hachioji (JP)

(73) Assignee: Olympus Corporation, Tokyo (JP)

( * ) Notice: Subject to any disclaimer, the term of this patent is extended or adjusted under 35 U.S.C. 154(b) by 58 days.

(21) Appl. No.: 10/437,600

(22) Filed: May 14, 2003

(65) Prior Publication Data

US 2003/0216723 A1 Nov. 20, 2003

(30) Foreign Application Priority Data

May 17, 2002 (JP) ............... 2002-142698

(51) Int. Cl.
*A61B 18/00* (2006.01)
*H01R 13/73* (2006.01)

(52) U.S. Cl. .................. 606/34; 128/898; 439/894

(58) Field of Classification Search .......... 606/32–41; 439/105
See application file for complete search history.

(56) References Cited

U.S. PATENT DOCUMENTS

| | | | | |
|---|---|---|---|---|
| 3,566,872 A * | 3/1971 | Draeger et al. ............. | 128/897 |
| 5,048,941 A * | 9/1991 | Hamada et al. ............. | 359/368 |
| 5,122,904 A * | 6/1992 | Fujiwara et al. ............. | 359/510 |
| 5,349,137 A * | 9/1994 | Cedrone ................... | 174/76 |
| 5,557,210 A * | 9/1996 | Cappa et al. ............... | 324/539 |
| 5,591,119 A * | 1/1997 | Adair ...................... | 600/112 |
| 5,762,525 A * | 6/1998 | Candeloro ................. | 439/660 |
| 5,790,307 A * | 8/1998 | Mick et al. ................ | 359/382 |
| 5,873,814 A * | 2/1999 | Adair ...................... | 600/109 |
| 5,891,020 A * | 4/1999 | Luber et al. ............... | 600/300 |
| 6,139,341 A * | 10/2000 | Hun ....................... | 439/172 |
| 6,183,299 B1 * | 2/2001 | Ward et al. ................ | 439/595 |
| 6,318,864 B1 * | 11/2001 | Fukaya et al. ............. | 359/510 |
| 6,398,721 B1 | 6/2002 | Nakamura et al. | |
| 6,441,958 B1 * | 8/2002 | Yeung et al. .............. | 359/372 |
| 6,793,517 B1 * | 9/2004 | Neer et al. ................ | 439/372 |
| 6,805,453 B1 * | 10/2004 | Spetzler et al. ............ | 359/510 |
| 2001/0012732 A1 * | 8/2001 | Kitchens .................. | 439/622 |
| 2001/0019907 A1 * | 9/2001 | Glad et al. ................ | 439/131 |

FOREIGN PATENT DOCUMENTS

| | | |
|---|---|---|
| EP | 1124150 A1 * | 8/2001 |
| JP | 2000-210302 | 8/2000 |
| JP | 2001-208978 | 8/2001 |

* cited by examiner

*Primary Examiner*—Henry M. Johnson, III
(74) *Attorney, Agent, or Firm*—Scully, Scott, Murphy & Presser PC (57) ABSTRACT

An operation system and a connecting adapter are provided. The operation system includes an operation microscope, an external device connectable to the operation microscope, and a connecting adapter for electrically connecting the operation microscope and the external device without bringing the operation microscope and the external device into contact with each other, which maintains a state of sterilization of the external device.

16 Claims, 5 Drawing Sheets

OPERATION SYSTEM AND MOUNTING DEVICE FOR EXTERNAL DEVICE FOR USE IN THE OPERATION SYSTEM

CROSS REFERENCE TO RELATED APPLICATION

This invention claims the priority of Japanese patent application No. 2002-142,698, filed May 17, 2002, in Japan, the contents of which is hereby incorporated by reference.

BACKGROUND OF THE INVENTION

1. Field of the Invention

The present invention relates to an operation system and a mounting device for an external device for use in the operation system.

2. Description of the Related Art

In recent years, operation microscope systems have been developed which enable operators to use operation microscopes together with other medical instruments (external devices) such as operation devices. For example, there is an operation microscope system which enables an operator to use both an operation microscope and an endoscope so that the operator observes a blind-spot area unobservable with the operation microscope under observation with the operation microscope, and there is also an operation microscope system which enables an operator to use both an operation microscope and an operation device such as an electrical scalpel for performing treatment on a site of operation.

Throughout an operation, the vicinity of a site of operation is maintained as a clean area which is free of bacterial contamination. A power source or a control part of an operation device is in general disposed in an unclean area (wherein a certain degree of bacterial contamination is allowed), and is generally arranged at a position distant from the site of operation.

In general, it is difficult to sterilize or disinfect an operation microscope itself to be used during operation. For this reason, the operation microscope when in use is fitted with a sterilization drape which is a cover for covering its entire microscope body disposed in the unclean area, in order that the sterilization of the external surface of the microscope body located in the vicinity of a site of operation can be ensured. In the case where an operator is to insert an external device such as an endoscope or a therapeutic instrument into a site of operation and manipulate the external device to perform a medical act such as observation or treatment under observation with the operation microscope, the operator holds the external device by hand and guides the external device toward the site of operation under microscopic observation (under optical observation).

It is desirable that the external device be kept away from the site of operation or easily removed from the operation microscope when the operator temporarily stops using the external device or changes the position and the observing direction of the microscope body of the operation microscope according to the state of progress of an operation.

For example, an operation system which uses both an operation microscope and an electrically driven operation device is disclosed in JP-A-2000-210302. In this operation system, signal lines for supplying electrical power to the operation device are disposed in the inside of the operation microscope. The microscope body of the operation microscope is provided with an electrically connecting portion to which a connector part of the operation device can be electrically connected.

In this operation system, electrical power is supplied to the operation device when a connector part of an electric cord of the operation device to be used in a clean area (free of bacteria) near a site of operation is connected to the electrically connecting portion of the microscope body of the operation microscope disposed in an unclean area. Accordingly, in general, the connector part of the electric cord of the operation microscope need not be directly connected to the power source section of the operation microscope disposed in the unclean area distant from the site of operation, so that when the operator is to use the operation device, the operator alone can perform the process of connecting the connector part of the electric cord, and can easily perform the set-up process of the operation device.

An operation microscope system which uses both an operation microscope and auxiliary observing means (fiber scope) for observing a blind spot of the operation microscope is disclosed in JP-A-2001-208978. In this operation microscope system, there is shown a construction where a connector part of the auxiliary observing means for observing a blind spot of the operation microscope is optically connected to the microscope body of the operation microscope disposed in an unclean area, via a sterilizable adapter. Accordingly, the auxiliary observing means disposed in the clean area is constructed to be spatially separable from and optically connectable to the microscope body of the operation microscope disposed in the unclean area.

In this operation microscope system, a connector part of the fiber scope which is the auxiliary observing means used in the clean area near a site of operation and required to be retained in a sterilized state and the operation microscope disposed in the unclean area are connected to each other via the sterilizable adapter, whereby the auxiliary observing means and the operation microscope are prevented from coming into direct contact with each other. Accordingly, even if the auxiliary observing means is removed or mounted during operation, the state of sterilization of the auxiliary observing means can be ensured.

SUMMARY OF THE INVENTION

The invention provides an operation system and a connecting adapter therefor. The operation system includes an operation microscope, an external device connectable to the operation microscope, and a connecting adapter for electrically connecting the operation microscope and the external device without bringing the operation microscope and the external device into contact with each other, and can maintain the state of sterilization of the external device.

Further aspects of the invention will become apparent from the following description of drawings and examples.

DETAILED DESCRIPTION OF THE EXAMPLES OF THE INVENTION

Figure 1:
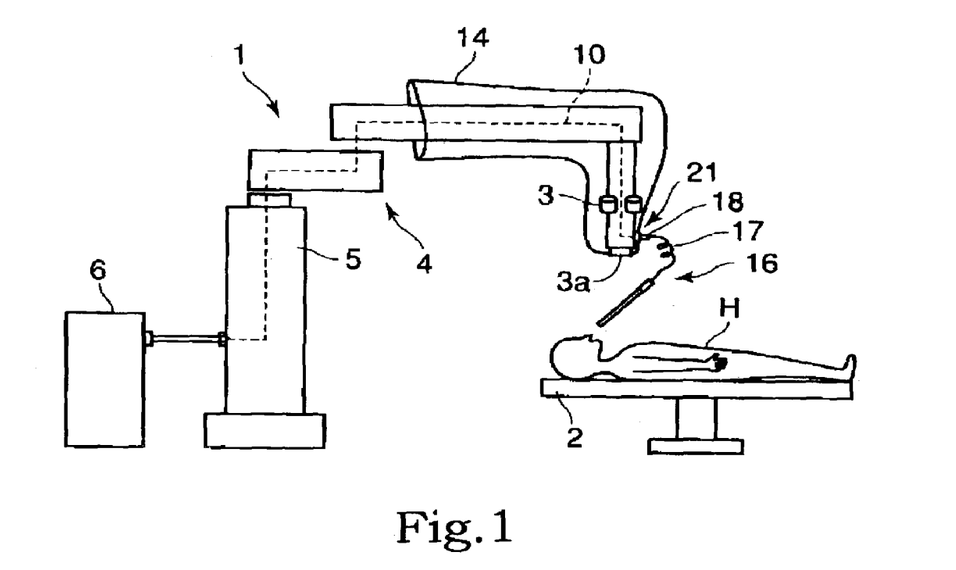
FIG. 1 is a side view showing a schematic construction of the whole of an operation system according to a first example of the invention.
Figure 2:
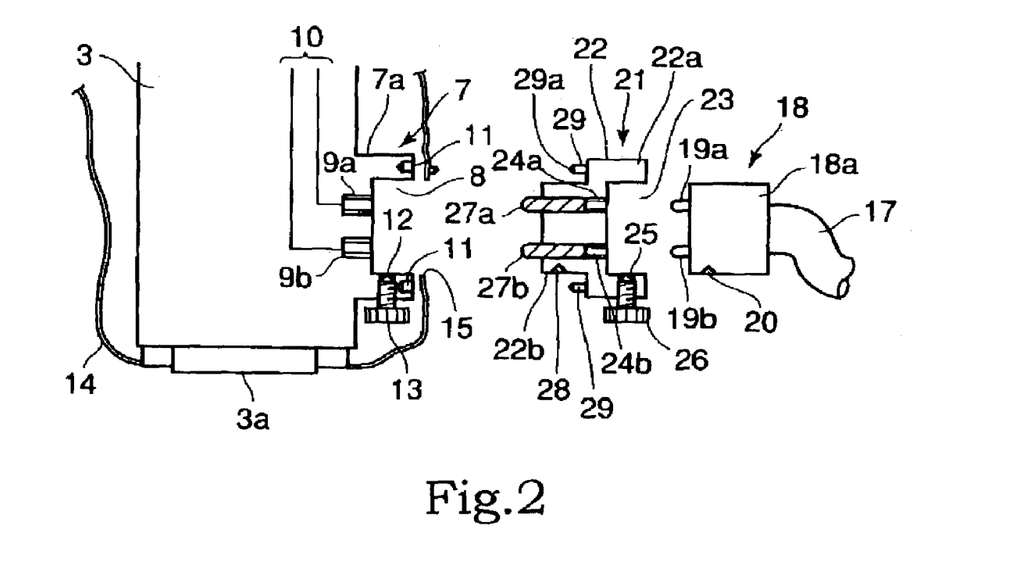
FIG. 2 is a longitudinal sectional view showing the state in which a connecting adapter is not yet connected in the operation microscope according to the first example.
Figure 3:
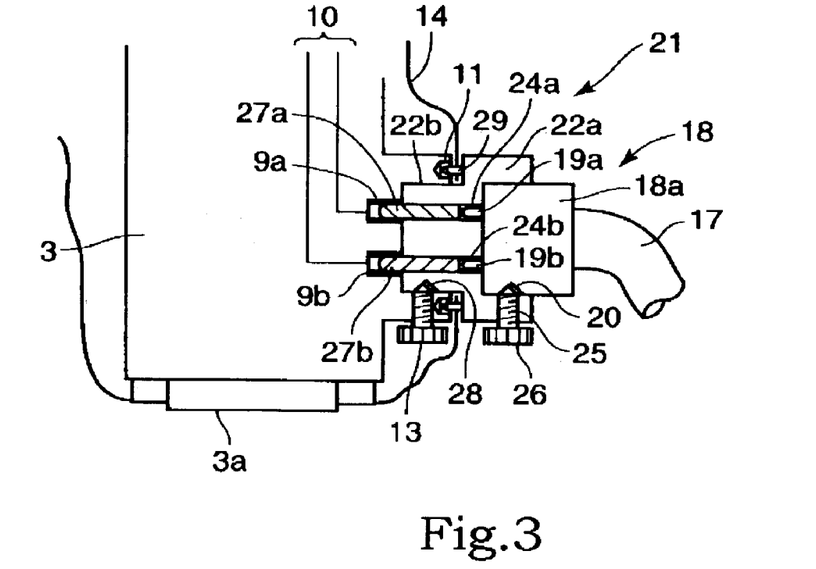
FIG. 3 is a longitudinal sectional view showing the state in which the connecting adapter is connected in the operation system according to the first example.

FIGS. 1 to 3 are views showing a first example. FIG. 1 shows a schematic construction of the whole of an operation system disposed in an operating room. In FIG. 1, reference numeral 1 denotes an operation microscope, and reference numeral 2 denotes a bed. The operation microscope 1 chiefly includes a microscope body 3 having an observing optical system for enabling an operator to observe at a magnified scale the area of a patient H that is to be submitted to an operation on the bed 2, i.e., the site of operation of the patient H, an arm section 4 capable of three-dimensionally moving and fixing the microscope body 3, and a support section 5. A power supply section 6 for supplying electrical power to the operation microscope 1 is connected to the support section 5.

In addition, an objective optical system 3a is disposed at the bottom of the microscope body 3. As shown in FIG. 2, an external device connecting part 7 is provided on the peripheral wall of the microscope body 3. A protruding portion 7a which protrudes outwardly from the peripheral wall of the microscope body 3 is provided on the external device connecting part 7. A circular mounting hole 8 is formed in the end face of the protruding portion 7a.

Two contacts (electrically connecting portions) 9a and 9b each having a cylindrical hole-like shape are provided at the inside bottom of the mounting hole 8. A cable 10 which is arranged through the inside of the operation microscope 1 is connected at one end to the contacts 9a and 9b. The other end of the cable 10 is connected to the power supply section 6.

A plurality of pin recessing holes 11 are formed in the end face of the protruding portion 7a of the external device connecting part 7 in such a manner as to be spaced apart around the mounting hole 8. These pin recessing holes 11 are disposed concentrically around the mounting hole 8. A screw hole 12 is formed in a lower portion of the protruding portion 7a in such a manner as to extend in a direction approximately perpendicular to the central axis of the mounting hole 8. A mounting screw 13 is screwed into the screw hole 12 from below.

The operation microscope 1 is fitted with a sterilization drape 14 which is a cover for covering the entire periphery of the microscope body 3. This sterilization drape 14 is made of a material such as vinyl, and is fitted in the state of covering the operation microscope 1 from the microscope body 3 to the end portion of the arm section 4. An opening 15 which has approximately the same size as the mounting hole 8 is formed in the sterilization drape 14 at a position corresponding to the mounting hole 8 of the microscope body 3.

In this operation system, an electrical scalpel 16 which is a sterilizable operation device for treating the site of operation is provided as a medical instrument for use with the operation microscope 1. An electrically driven section (which is not shown) is provided in the inside of the electrical scalpel 16. One end of an electric cable 17 for supplying electricity to the electrically driven section is connected to the proximal end of the electrical scalpel 16. A connector part 18 is provided integrally with the other end of the electric cable 17.

This connector part 18 is provided with a connector part body 18a formed in a shape corresponding to the mounting hole 8 of the microscope body 3. Two contact pins 19a and 19b for electrical connection are protruded from the end face of the connector part body 18a. The contact pins 19a and 19b are arranged at positions corresponding to the respective two contacts 9a and 9b of the mounting hole 8 of the microscope body 3. The contact pins 19a and 19b are connected to the electrically driven section (not shown) in the electrical scalpel 16 via the electric cable 17. An engaging detent 20 having an approximately conical shape is formed in the peripheral face of the connector part body 18a on a side closer to the end face of the connector part body 18a.

The connector part 18 of the electrical scalpel 16 is mounted onto the external device connecting part 7 of the operation microscope 1 via a connecting adapter (connecting means) 21. This connecting adapter 21 has an adapter body portion 22 formed of a material having electrical insulating properties. This adapter body portion 22 is provided with a first mounting portion 22a having approximately the same outside diameter as the protruding portion 7a of the microscope body 3, and a second mounting portion 22b having approximately the same outside diameter as the inside diameter of the mounting hole 8 of the microscope body 3 (an outside diameter smaller than the outside diameter of the protruding portion 7a).

A circular mounting hole 23 having the same size as the mounting hole 8 of the microscope body 3 is formed in the end face of the first mounting portion 22a. Two contacts (contact portions) 24a and 24b each having a cylindrical hole-like shape for electrical connection are provided at the inside bottom of the mounting hole 23. The contacts 24a and 24b are arranged at positions corresponding to the respective two contact pins 19a and 19b of the connector part 18 of the electrical scalpel 16.

A screw hole 25 is formed in a lower portion of the mounting portion 22a in such a manner as to extend in a direction approximately perpendicular to the central axis of the mounting hole 23. The screw hole 25 is arranged at a position corresponding to the engaging detent 20 of the connector part body 18a. A mounting screw 26 is screwed into the screw hole 25 from below. A pointed portion of the mounting screw 26 is brought into engagement with the engaging detent 20 of the connector part body 18a in the state of being inserted into the engaging detent 20.

The second mounting portion 22b of the connecting adapter 21 is formed to have approximately the same structure as the connector part 18 of the electrical scalpel 16. Namely, two contact pins (contact portions) 27a and 27b for electrical connection, each of which is made of a conductive material, are protruded from the end face of the second mounting portion 22b. The contact pins 27a and 27b are arranged at positions corresponding to the respective two contacts 9a and 9b of the mounting hole 8 of the microscope body 3. The proximal ends of the respective contact pins 27a and 27b are respectively connected to the contacts 24a and 24b each having a cylindrical hole-like shape. An engaging detent 28 having an approximately conical shape is formed in the peripheral face of the second mounting portion 22b on a side closer to the end face of the second mounting portion 22b.

A plurality of fixing pins 29 are concentrically protruded from a step between the first mounting portion 22a and the second mounting portion 22b of the connecting adapter 21. Cone-shaped portions 29a are respectively formed at ends of the fixing pins 29. When the second mounting portion 22b of the connecting adapter 21 is mounted into the mounting hole 8 of the microscope body 3, the cone-shaped portions 29a of the respective fixing pins 29 are inserted through the sterilization drape 14 into the pin recessing holes 11 which are spaced apart around the mounting hole 8. The opening 15 of the sterilization drape 14 is set to have a shape (size) which is larger than the outside diameter of the second mounting portion 22b of the connecting adapter 21 and is smaller than the diameter of a circle around which the fixing pins 29 are spaced apart at the step between the first mounting portion 22a and the second mounting portion 22b of the connecting adapter 21.

The function of the first example will be described below. When this operation system is to be used, first of all, an operator covers the operation microscope 1 with the sterilization drape 14 in such a manner as to cover the whole of the microscope body 3 and a part of the arm section 4. Then, the operator performs the process of positioning the opening 15 of the sterilization drape 14 with respect to the mounting hole 8 of the microscope body 3 and connecting the connector part 18 of the electrical scalpel 16 to the external device connecting part 7 of the microscope body 3 of the operation microscope 1 via the sterilized connecting adapter 21. At this time, as will be described below, the second mounting portion 22b of the connecting adapter 21 is connected to the external device connecting part 7 of the microscope body 3, while the connector part 18 of the electrical scalpel 16 is connected to the first mounting portion 22a of the connecting adapter 21.

Namely, in the case where the second mounting portion 22b of the connecting adapter 21 is to be connected to the external device connecting part 7 of the microscope body 3, after the second mounting portion 22b of the connecting adapter 21 has been inserted into the opening 15 of the sterilization drape 14, the second mounting portion 22b is removably inserted into the mounting hole 8 of the microscope body 3. Then, the contact pins 27a and 27b for electrical connection, which are protruded from the second mounting portion 22b inserted into the mounting hole 8, are respectively removably inserted into the contacts 9a and 9b each having a cylindrical hole-like shape in the mounting hole 8, whereby electrical connection is established between each of the contact pins 27a and 27b and the corresponding one of the contacts 9a and 9b.

At the same time, the cone-shaped portion 29a of each of the fixing pins 29 is inserted through the sterilization drape 14 into the corresponding one of the pin recessing holes 11 spaced apart around the mounting hole 8. In this manner, the edge portion of the opening 15 of the sterilization drape 14 is fixed in the state of being clamped between the connecting adapter 21 and the end face of the external device connecting part 7 of the microscope body 3, thereby forming sterilization retaining means.

Then, the mounting screw 13 is screwed with the respective contact pins 27a and 27b for electrical connection which are protruded from the second mounting portion 22b being inserted in the contacts 9a and 9b each having a cylindrical hole-like shape in the mounting hole 8, whereby the point portion of the mounting screw 13 is brought into engagement with the engaging detent 28 of the second mounting portion 22b in the state of being inserted in the engaging detent 28. In this manner, the microscope body 3 and the connecting adapter 21 are fixed to each other.

When the electrical scalpel 16 is to be used, the operator inserts the connector part 18 of the electrical scalpel 16 into the mounting hole 23 of the connecting adapter 21. At this time, the contact pins 19a and 19b for electrical connection, which are protruded from the connector part 18 inserted in the mounting hole 23, are removably inserted into the respective two contacts 24a and 24b each having a cylindrical hole-like shape in the mounting hole 23. In this manner, the contact pins 19a and 19b for electrical connection which are protruded from the connector part 18 are fitted in the state of being inserted in the respective two contacts 24a and 24b each having a cylindrical hole-like shape in the mounting hole 23, whereby electrical connection is established between each of the contact pins 19a and 19b and the corresponding one of the contacts 24a and 24b.

Then, when the mounting screw 26 is screwed, the point portion of the mounting screw 26 is brought into engagement with the engaging detent 20 of the connector part body 18a in the state of being inserted into the engaging detent 20. In this manner, the connecting adapter 21 and the connector part 18 are fixed to each other.

When the connector part 18 of the electrical scalpel 16 is connected to the external device connecting part 7 of the microscope body 3 of the operation microscope 1 via the connecting adapter 21, electrical power from the power supply section 6 and control signals pass through the cable 10, the contacts 9a and 9b, the contact pins 27a and 27b, the contacts 24a and 24b, the contact pins 19a and 19b and the electric cable 17 in named order, and are supplied to the electrically driven section (not shown) in the inside of the electrical scalpel 16. In this manner, the connector part 18 and the contact pins 19a and 19b all of which are disposed in the clean area and the power supply section 6 and the contacts 9a and 9b all of which are disposed in the unclean area are electrically connected to one another without being brought into direct contact with one another. Accordingly, the sterilized state of the connector part 18 of the mounting hole 8 is ensured.

During this state, the operator switches on and off the supply of electrical power to the electrical scalpel 16 while manipulating a switch which is not shown. In this manner, the electrical scalpel 16 is driven, and a medical act such as treatment is performed on the patient H by the operator.

In the case where the operator is to change the position of the microscope body 3 of the operation microscope 1 or does not need to use the electrical scalpel 16 for a long time during operation, the operator unfastens the mounting screw 26 and pulls the point portion of the mounting screw 26 out of the engaging detent 20 of the connector part 18. Subsequently, the operator removes the connector part 18 by pulling the connector part 18 by hand out of the connecting adapter 21.

Incidentally, if the operator is to use the electrical scalpel 16 again, the operator connects the connector part 18 to the connecting adapter 21 in a sequence similar to the above-described one.

The first example serves the following advantages. Namely, in this operation system, the connector part 18 of the electrical scalpel 16 is removably connected to the external device connecting part 7 of the microscope body 3 of the operation microscope 1 via the sterilized connecting adapter 21. During this time, through the contact pins 27a and 27b and the contacts 24a and 24b of the connecting adapter 21, electrical conduction is established between each of the contact pins 19a and 19b of the connector part 18 of the electrical scalpel 16 and the corresponding one of the contacts 9a and 9b of the microscope body 3 of the operation microscope 1 which are connected to a power source in the power supply section 6 via the cable 10. Accordingly, the state of sterilization near the microscope body 3 can be ensured easily and inexpensively.

In addition, the opening 15 is provided in the sterilization drape 14 which covers the microscope body 3 of the operation microscope 1, and the fixing pins 29 for fixing the sterilization drape 14 is provided on the connecting adapter 21, and further, the pin recessing holes 11 are provided in the external device connecting part 7 of the microscope body 3. Accordingly, even if the operator performs a movement of the microscope body 3 or any other manipulation, the opening 15 of the sterilization drape 14 does not undergo a positional deviation and the microscope body 3 is not exposed to the outside of the sterilization drape 14, so that the sterilization (the state of sterilization) near the microscope body 3 is prevented from being impaired.

Incidentally, although the above description of the first example has referred to the example using the sterilization drape 14 which covers the whole of the microscope body 3, a sterilization cap of the type which is generally used during ophthalmological operation or the like in order to cover only a manipulating part to be manipulated during operation may also be used. In this case as well, it is possible to achieve a construction which enables the sterilizable operation device (the electrical scalpel 16) to be removably connected to the microscope body 3 via the sterilizable connecting adapter 21, whereby it is possible to achieve the advantage of ensuring the sterilization of the operation device at any time.

In addition, in the first example, the mounting hole 23 provided in the connecting adapter 21 is formed to have the same size as the mounting hole 8 of the microscope body 3, and the second mounting portion 22b of the connecting adapter 21 is formed to have approximately the same structure as the connector part 18 of the electrical scalpel 16., Accordingly, the second mounting portion 22b of the connecting adapter 21 can be mounted into the connector mounting hole 8 provided in the microscope body 3, and a connector (the connector part 18) extending from the operation device can be mounted into the mounting hole 23 of the connecting adapter 21. Accordingly, it is possible to use the connecting adapter 21 without the need to perform any change on a connector mounting portion of the operation microscope 1 nor on the connector extending from the operation device, whereby it is possible to easily ensure the sterilization of the operation system and the operation microscope 1.

Figure 4:
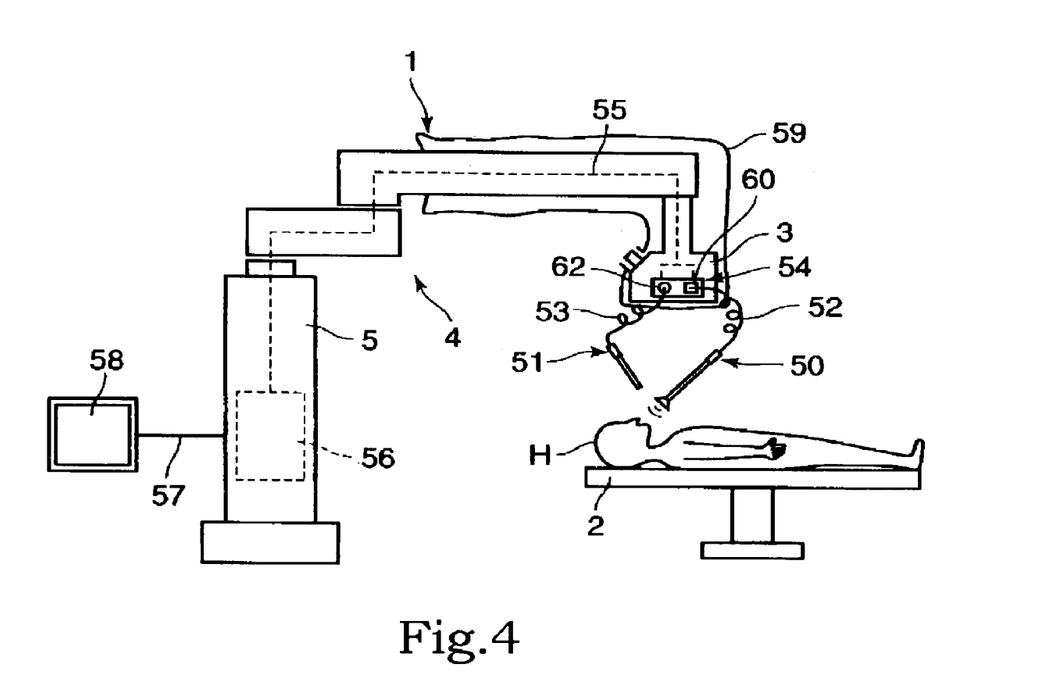
FIG. 4 is a side view showing a schematic construction of the whole of an operation system according to a second example of the invention.
Figure 5:
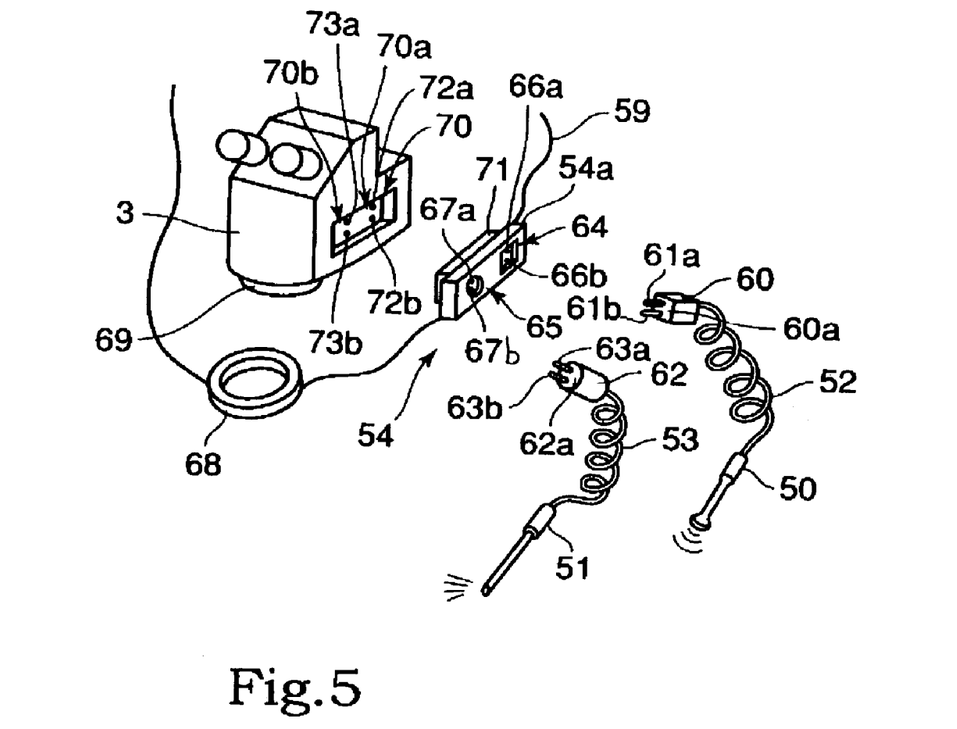
FIG. 5 is a perspective view showing the state in which a connecting adapter is not yet connected in the operation microscope according to the second example.
Figure 6:
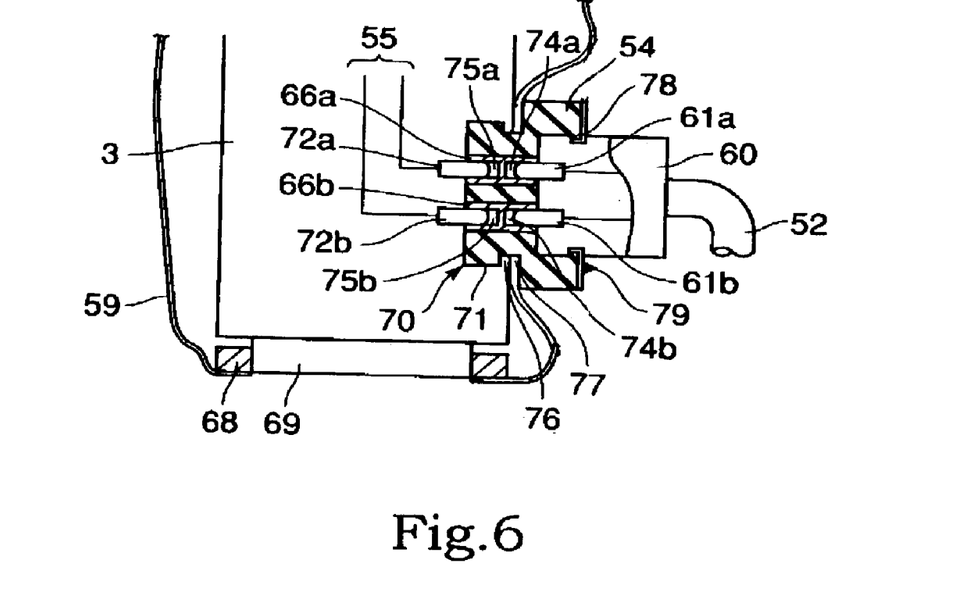
FIG. 6 is a longitudinal sectional view showing the state in which the connecting adapter is connected in the operation microscope according to the second example.

FIGS. 4 to 6 show a second example. The construction of the second example is such that the construction of the operation system of the first example is modified as follows. In FIGS. 4 to 6, the same reference numerals are used to denote the same sections, parts and portions as those of the first example, and the same description is omitted.

In the operation system of the second example, an ultrasonic probe 50 which is an operation device having an electrically driven section, and an electronic endoscope 51 are used as external devices to be connected to the operation microscope 1.

The ultrasonic probe 50 contains the electrically driven section for enabling ultrasonic observation, such as an ultrasonic vibrator which is not shown. One end of a cable 52 is connected to the proximal end of the ultrasonic probe 50. As shown in FIG. 5, a connector 60 is connected to the other end of the cable 52. An end face 60a of the connector 60 is formed into, for example, an approximately rectangular shape. Contact pins 61a and 61b for electrical connection are protruded from the end face 60a of the connector 60. These contact pins 61a and 61b are connected to the electrically driven section such as an ultrasonic vibrator (not shown) in the inside of the ultrasonic probe 50 via the cable 52.

The electronic endoscope 51 contains an objective optical system, illuminating means and image pickup means as is well known in the art. One end of a cable 53 is connected to the proximal end of the electronic endoscope 51. A connector 62 is connected to the other end of the cable 53. An end face 62a of the connector 62 is formed into, for example, an approximately circular shape which differs from the approximately rectangular shape of the end face 60a of the connector 60 of the ultrasonic probe 50. Contact pins 63a and 63b for electrical connection are protruded from the end face 62a of the connector 62. These contact pins 63a and 63b are connected to the illuminating means and the image pickup means (not shown) in the inside of the ultrasonic probe 51 via the cable 53.

A control part 56 is contained in the support section 5 of the operation microscope 1. An external monitor 58 is connected to the control part 56 via a video cable 57. The monitor 58 is capable of displaying an observed image of the patient H who is observed with the ultrasonic probe 50 or whose image is picked up with the electronic endoscope 51.

A mounting concave portion 70 to which an external device is to be connected is provided in the peripheral wall of the microscope body 3. Two external-device connecting portions 70a and 70b are arranged side by side at the inside bottom of the mounting concave portion 70. The external-device connecting portion 70a is provided with two contacts 72a and 72b, while the external-device connecting portion 70b is provided with two contacts 73a and 73b. The contacts 72a, 72b, 73a and 73b are connected to the control part 56 via a cable 55 arranged through the arm section 4.

The microscope body 3 and a part of the arm section 4 of the operation microscope 1 are covered with a sterilization drape 59 which is a cover made of a sterilizable material such as vinyl. A connecting adapter 54 and an objective lens hood 68 are integrally secured to the sterilization drape 59 by an adhesive or the like so that the state of sterilization is ensured.

The connecting adapter 54 has an adapter body 54a made of an elastic material such as sterilizable, electrically non-conductive rubber. Examples of the elastic material are silicon rubber and fluororubber which are sterilizable with ethylene oxide gas. Two mounting concave portions 64 and 65 to which an external device is to be connected are arranged side by side on the front face of the adapter body 54a. The mounting concave portion 64 is formed as a rectangular concave portion approximately similar to the connector 60 of the ultrasonic probe 50. The mounting concave portion 64 is provided with contact receiving portions 66a and 66b each made of an electrically conductive material. These contact receiving portions 66a and 66b are disposed at positions where the contact receiving portions 66a and 66b are respectively opposed to the contact pins 61a and 61*b* of the connector 60 when the connector 60 is inserted into the mounting concave portion 64.

The other mounting concave portion 65 is formed as a circular concave portion approximately similar to the connector 62 of the electronic endoscope 51. The mounting concave portion 65 is provided with contact receiving portions 67*a* and 67*b* each made of an electrically conductive material. These contact receiving portions 67*a* and 67*b* are disposed at positions where the contact receiving portions 67*a* and 67*b* are respectively opposed to the contact pins 63*a* and 63*b* of the connector 62 when the connector 62 is inserted into the mounting concave portion 65.

A connecting convex portion 71 which is formed in a shape corresponding to the mounting concave portion 70 of the microscope body 3 is protruded from the reverse face of the connecting adapter 54. The connecting convex portion 71 is protruded into the inside of the sterilization drape 59.

The objective lens hood 68 is formed in a shape corresponding to an objective lens frame 69 of the microscope body 3. The objective lens hood 68 can be fitted onto the periphery of the objective lens frame 69 of the microscope body 3 without clearance as shown in FIG. 6.

The connecting convex portion 71 of the connecting adapter 54 is removably fitted into the mounting concave portion 70 of the microscope body 3. In this manner, the connecting adapter 54 is removably connected to the mounting concave portion 70 of the microscope body 3.

As shown in FIG. 6, the contact receiving portion 66*a* in the mounting concave portion 64 of the connecting adapter 54 has a first contact hole 74*a* formed on its front side and a second contact hole 75*a* formed on its back side, and the contact receiving portion 66*b* in the mounting concave portion 64 of the connecting adapter 54 has a first contact hole 74*b* formed on its front side and a second contact hole 75*b* formed on its back side. The first contact holes 74*a* and 74*b* are respectively formed in shapes which enable the respective contact pins 61*a* and 61*b* to be fitted into the first contact holes 74*a* and 74*b* when the connector 60 is inserted into the mounting concave portion 64. Similarly, the second contact holes 75*a* and 75*b* are respectively formed in shapes which enable the respective contacts 72*a* and 72*b* to be fitted into the second contact holes 75*a* and 75*b* when the connecting adapter 54 is inserted into the mounting concave portion 70.

Incidentally, the contact receiving portions 67*a* and 67*b* in the mounting concave portion 65 of the connecting adapter 54 are also constructed similarly to the contact receiving portions 66*a* and 66*b* of the mounting concave portion 64.

An inwardly protruding portion 76 is formed to extend along the edge portion of the opening of the mounting concave portion 70. The inside diameter of the protruding portion 76 is set to be smaller than the inside diameter of the mounting concave portion 70. A mounting groove 77 which disengageably engages with the protruding portion 76 of the mounting concave portion 70 is formed to extend along the peripheral portion of the connecting convex portion 71 of the connecting adapter 54. The mounting groove 77 is provided at a position where the mounting groove 77 is opposed to the protruding portion 76 when the connecting convex portion 71 is inserted into the mounting concave portion 70.

An inwardly protruding portion 78 is formed to extend along the edge portion of the opening of the mounting concave portion 64 of the connecting adapter 54. The inside diameter of the protruding portion 78 is set to be smaller than the inside diameter of the mounting concave portion 64. A mounting groove 79 which disengageably engages with the protruding portion 78 of the mounting concave portion 64 is formed to extend along the peripheral portion of the connector 60. The mounting groove 79 is provided at a position where the mounting groove 79 is opposed to the protruding portion 78 when the connector 60 is inserted into the mounting concave portion 64.

Incidentally, the magnitude of force required during the process of pulling (removing) from the mounting concave portion 70 the connecting convex portion 71 of the connecting adapter 54 that is fitted in the mounting concave portion 70 is set to a value sufficiently larger than the magnitude of force required during the process of pulling from the mounting concave portion 64 of the connecting adapter 54 the connector 60 fitted in the mounting concave portion 64 of the connecting adapter 54.

The function of the second example will be described below. When this operation microscope 1 is to be used, first of all, an operator covers the operation microscope 1 with the sterilized sterilization drape 59 in such a manner as to cover the microscope body 3 and the arm section 4. After that, as shown in FIG. 6, the operator fits the objective lens hood 68 of the sterilization drape 59 onto the periphery of the objective lens frame 69 of the microscope body 3.

Then, the operator pushes the connecting convex portion 71 of the connecting adapter 54 provided integrally with the sterilization drape 59 into the mounting concave portion 70 of the microscope body 3. During the process of pushing the connecting convex portion 71, the connecting convex portion 71 made of an elastic material such as rubber is pushed into the mounting concave portion 70 while undergoing elastic deformation in a compressed state by being pressed by the protruding portion 76 of the edge portion of the mounting concave portion 70. When the connecting adapter 54 in this state is inserted into the mounting concave portion 70, at the time when the mounting groove 77 of the connecting adapter 54 is inserted up to a position corresponding to the protruding portion 76, the elastic deformation of the connecting convex portion 71 is recovered and the protruding portion 76 is fitted into the mounting groove 77. In this manner, the connecting adapter 54 is fixed to the mounting concave portion 70 of the microscope body 3.

During the mounting of the connecting adapter 54, at the same time as the process of mounting the connecting adapter 54, the contacts 72*a* and 72*b* of the mounting concave portion 70 are respectively fitted into the second contact holes 75*a* and 75*b* of the contact receiving portions 66*a* and 66*b* of the connecting adapter 54, and the respective contact receiving portions 66*a* and 66*b* are electrically connected to the contacts 72*a* and 72*b*. At the same time, the respective contact receiving portions 67*a* and 67*b* are similarly electrically connected to the contacts 73*a* and 73*b* of the mounting concave portion 70.

When the ultrasonic probe 50 is to be used, the operator pushes the connector 60 into the mounting concave portion 64 of the connecting adapter 54 so that the connector 60 is fitted into the mounting concave portion 64. During the process of pushing the connector 60 into the mounting concave portion 64 of the connecting adapter 54, the protruding portion 78 of the edge portion of the mounting concave portion 64 is elastically deformed into the state of being spread out by being pressed by the end face 60*a* of the connector 60. When the connector 60 in this state is further inserted into the mounting concave portion 64, at the time when the mounting groove 79 of the connector 60 is inserted up to a position corresponding to the protruding portion 78, the elastic deformation of the protruding portion 78 of the mounting concave portion 64 is recovered and the protruding portion 78 is fitted into the mounting groove 79. In this manner, the connector 60 is fixed to the connecting adapter 54.

During the process of inserting the connector 60, at the same time as the fixation of the connector 60, the contact pins 61a and 61b of the connector 60 are respectively fitted into the first contact holes 74a and 74b of the contact receiving portions 66a and 66b, and the respective contact receiving portions 66a and 66b are electrically connected to the contact pins 61a and 61b.

In this manner, the electrically driven section (not shown) of the ultrasonic probe 50 is connected to the control part 56 contained in the support section 5 of the operation microscope 1, and supplies electrical power and control signals to the ultrasonic probe 50 via the cable 52, the contact pins 61a and 61b, the contact receiving portions 66a and 66b, the contacts 72a and 72b and the cable 55 in named order.

During this state, the operator holds the ultrasonic probe 50 by hand, and brings the ultrasonic probe 50 into contact with a site of operation of the patient H while observing the site of operation through the operation microscope 1. At this time, an observed image of the site of operation is transmitted from the electrically driven section (not shown) of the ultrasonic probe 50 to the monitor 58 via the control part 56 and the video cable 57, and is displayed on the screen of the monitor 58. In this manner, the operator carries out ultrasonic observation. The control part 56 outputs various control signals for controlling the function and action of the ultrasonic probe 50, and carries out control of the various kinds required to display on the monitor 58 the output signal obtained from the ultrasonic probe 50.

When the operator is to change the position of the operation microscope 1 or to stop using the ultrasonic probe 50, the operator pulls the connector 60 of the ultrasonic probe 50 from the mounting concave portion 64 of the connecting adapter 54. Then, the operator places the ultrasonic probe 50 at a position which does not hinder the operation, and continues the manipulation of the operation microscope 1 and operation processes.

When the operator is to use the electronic endoscope 51, the operator fits the connector 62 into the mounting concave portion 65 similarly to the case of use of the ultrasonic probe 50. Through the process of connecting the connector 62, the respective contact receiving portions 67a and 67b of the connecting adapter 54 are electrically connected to the contact pins 63a and 63b of the connector 62.

In this manner, the objective optical system, the illuminating means and the image pickup means (none of which is shown) provided in the inside of the electronic endoscope 51 are electrically connected to the control part 56 contained in the support section 5 of the operation microscope 1, via the cable 53, the contact pins 63a and 63b, the contact receiving portions 67a and 67b, the contacts 73a and 73b and the cable 55 in named order, whereby electrical power and control signals are connected to the electronic endoscope 51.

During this state, the operator holds the electronic endoscope 51 by hand and observes a desired site of operation of the patient H through the operation microscope 1, and inserts the electronic endoscope 51 into the site of operation of the patient H under observation with the operation microscope 1 so that the operator can observe a blind-spot area of the operation microscope 1. At this time, an observed image picked up by the image pickup means of the electronic endoscope 51 is transmitted from the control part 56 to the monitor 58 via the video cable 57, and is displayed on the screen of the monitor 58. In this manner, the operator carries out endoscopic observation.

When the operator is to change the position of the operation microscope 1 or to stop using the electronic endoscope 51, the operator pulls the connector 62 of the electronic endoscope 51 from the mounting concave portion 65 of the connecting adapter 54. During this state, the operator places the electronic endoscope 51 at a position which does not hinder the operation, and continues operation processes such as the manipulation of the operation microscope 1.

In this example, although the ultrasonic probe 50 and the electronic endoscope 51 are used as external devices, the kinds of external devices which constitute the operation system together with the operation microscope 1 are not limited to these devices, and may also include electrically-driven operation devices such as cauteries and ultrasonic scalpels. In addition, although each of the above-described external devices has electrically connecting contacts provided at two positions, the number of positions is not limited to two.

The second example serves the following advantage. Namely, the sterilizable sterilization drape 59 which covers the microscope body 3 and the arm section 4 of the operation microscope 1 has the connecting adapter 54 integrally secured to the sterilization drape 59 by an adhesive or the like. Accordingly, the operator does not at all run the risk of touching an unclean area while fitting the connecting adapter 54 to the microscope body 3, and can also easily fit the connecting adapter 54 to the microscope body 3 without the need to take care to position the sterilization drape 59.

In addition, even if the operator mistakenly removes the connecting adapter 54 during operation, an unclean area such as the microscope body 3 is prevented from being exposed from the inside of the sterilization drape 59, so that there is no risk that the outside surface of the sterilization drape 59 may become unclean in the vicinity of the microscope body 3.

Furthermore, since the connecting adapter 54 has a plurality of mounting concave portions 64 and 65 into which external devices (the ultrasonic probe 50 and the electronic endoscope 51) can be fitted, the operator can carry out operation while using a plurality of external devices at the same time under observation with the operation microscope 1, whereby the efficiency of operation is improved.

Furthermore, the connector 60 of the ultrasonic probe 50 and the connector 62 of the electronic endoscope 51 have different shapes which allow the respective connectors 60 and 62 to be fitted into only the corresponding mounting concave portions 64 and 65. Accordingly, during the use of a plurality of external devices, the operator does not run the risk of mistakenly mounting either of the connectors 60 or 62 of the external devices into a wrong one of the mounting concave portions 64 and 65, and can, therefore, easily mount and remove such external devices.

Furthermore, the mounting concave portions 64 and 65 and the mounting concave portion 70 have different shapes and constitute a construction which does not allow the connector 60 and the connector 62 to be mounted to the microscope body 3 of the operation microscope 1 when the connecting convex portion 71 of the connecting adapter 54 is not fitted in the mounting concave portion 70. According to this construction, the operator is prevented from mistakenly fitting the connector 60 and the connector 62 into the mounting concave portion 70 when the connecting adapter 54 is not fitted, whereby the sterilization of each of the external devices and the operation microscope can be ensured.

Figure 7:
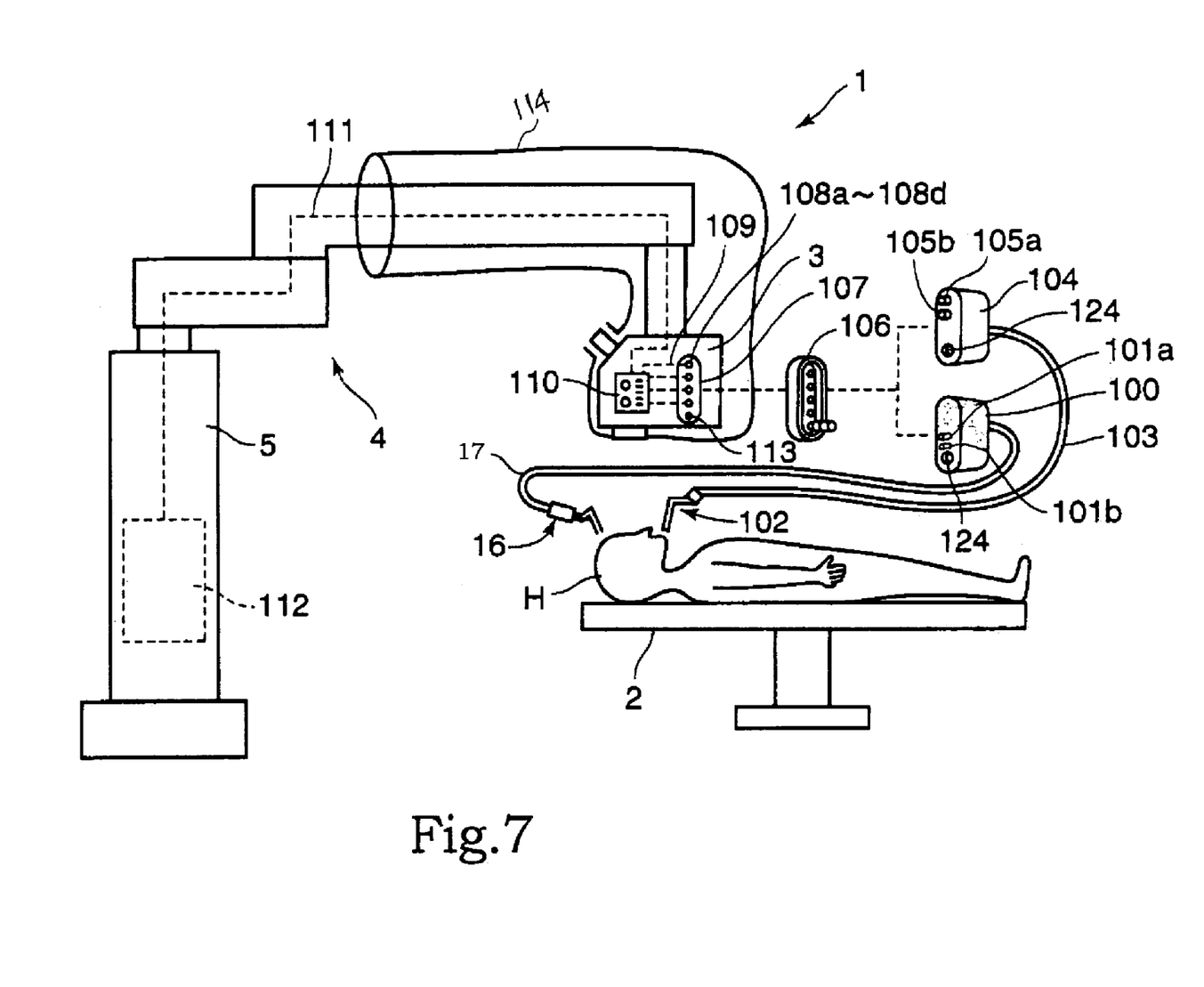
FIG. 7 is a side view showing a schematic construction of the whole of an operation system according to a third example of the invention.
Figure 8:
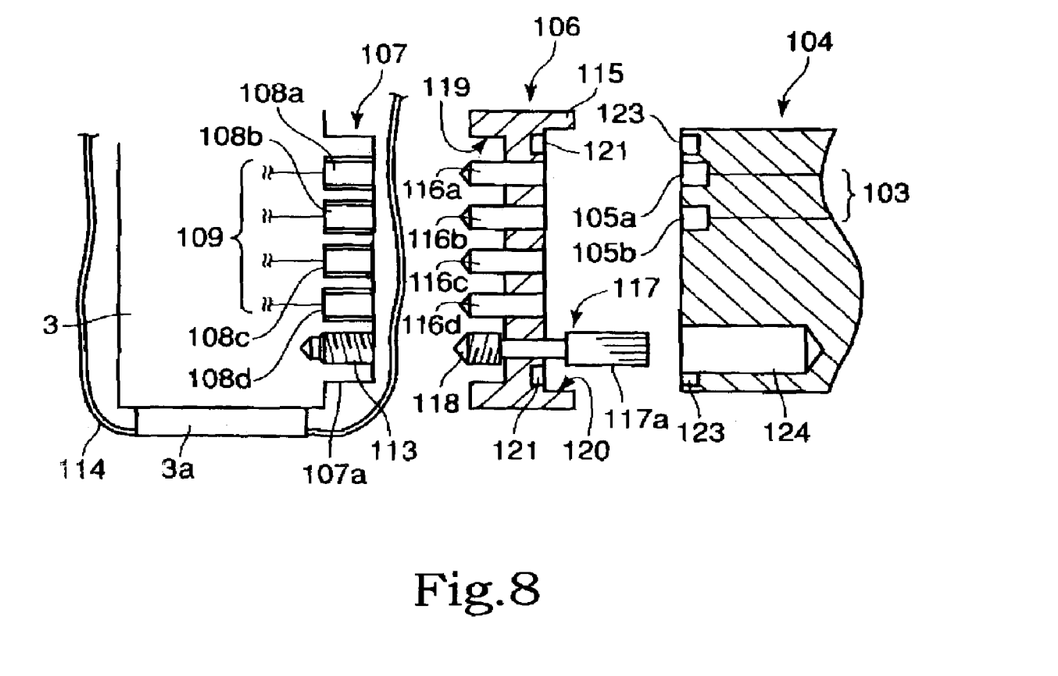
FIG. 8 is a longitudinal sectional view showing the state in which a connecting adapter is not yet connected in the operation microscope according to the third example.
Figure 9:
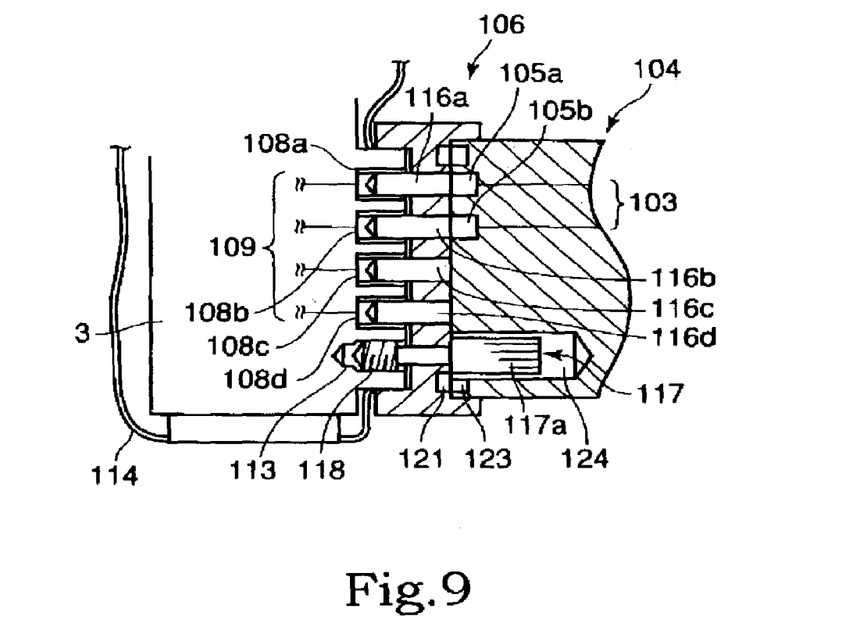
FIG. 9 is a longitudinal sectional view showing the state in which the connecting adapter is connected in the operation microscope according to the third example.

FIGS. 7 to 9 show a third example. In the third example, the construction of the operation system according to the first example is modified as follows. In FIGS. 7 to 9, the same reference numerals are used to denote the same sections, parts and portions as those of the first example, and the same description is omitted.

In the operation system of the third example, an electrical scalpel 16 which is a first operation device having an electrically driven section (not shown) and an ultrasonic scalpel 102 (refer to, for example, JP-A-9-299381) which is a second operation device having an electrically driven section (not shown) for ablating tissue at a therapeutic site by ultrasonic vibration are used as external devices to be connected to the operation microscope 1.

An external-device connecting portion 107 to which such external devices are to be connected and input means 110 are provided on the peripheral wall of the microscope body 3 of the operation microscope 1. The input means 110 includes at least one switch. As shown in FIG. 8, the external-device connecting portion 107 has a convex portion 107a which protrudes outwardly from the peripheral wall of the microscope body 3. A plurality of (in this example, four) contacts 108a to 108d each having an approximately cylindrical shape and one screw hole 113 are provided in the end face of the convex portion 107a. The contacts 108a to 108d and the input means 110 are interconnected via a cable 109 which is connected to the input means 110. Furthermore, the input means 110 is connected to control means 112 provided in the support section 5 via a cable 111 arranged through the arm section 4 and the support section 5.

The operator can appropriately control the input/output of each of the external devices by manipulating the switches provided in the input means 110. For example, in the case of the electrical scalpel 16, the operator can effect switching between an incision action and a coagulation action, i.e., selection of a function, by manipulating one of the switches. In the case of the ultrasonic scalpel 102, the operator can adjust the reach of the ultrasonic wave of the ultrasonic scalpel 102 by manipulating another of the switches and switching signals to be supplied to the ultrasonic scalpel 102. Incidentally, in the case where an electronic endoscope is used as an external device, the operator can manipulate one of the switches to allow and disallow control signals to be supplied from the control means 112 to the electronic endoscope, and to allow and disallow output signals from the electronic endoscope to be supplied to the control means 112. Through this manipulation, the operator can execute processes such as selecting one of the functions of an external device which is in use, allowing and disallowing control signals to be supplied from the control means 112, and allowing and disallowing signals to be supplied from the external device to the control means 112.

The construction in which this kind of input means is provided in the microscope body 3 makes it possible for the operator to directly and rapidly control the external devices without leaving a clean area.

The operation microscope 1 is fitted with a sterilization drape 114 which is a sterilizable cover made of vinyl chloride or the like and constructed to cover the entire periphery of the microscope body 3.

A connecting adapter 106 is removably connected to the convex portion 107a of the external-device connecting portion 107. The connecting adapter 106 has an adapter body 115 formed of a material having electrical insulating properties. Four contact pins 116a to 116d each made of a conductive material are integrally formed in the adapter body 115 in the state of being inserted through the adapter body 115 and arranged side by side. The respective contact pins 116a to 116d are provided at positions corresponding to the contacts 108a to 108d of the external-device connecting portion 107.

In addition, the point portions of the respective contact pins 116a to 116d are protruded outwardly from the adapter body 115, and cone-shaped portions are respectively formed at the points of the protruding portions of the contact pins 116a to 116d so that the points can pierce and be inserted through the sterilization drape 114.

The connecting adapter also has a mounting screw 117. A shank of the mounting screw 117 is inserted through and rotatably supported in the adapter body 115. The mounting screw 117 is arranged at a position where the mounting screw 117 is opposed to the screw hole 113 when the connecting adapter 106 is to be mounted to the external-device connecting portion 107 of the microscope body 3. Furthermore, a screw portion 118 to be screwed into the screw hole 113 of the microscope body 3 is provided at one end of the mounting screw 117. The point portion of the screw portion 118 has a conical shape so that the point portion can pierce and be inserted through the sterilization drape 114. The other end of the mounting screw 117 has a manipulating knob 117a.

A first mounting concave portion 119 having a concave shape capable of being removably fitted onto the convex portion 107a of the external-device connecting portion 107 of the microscope body 3 is provided in the front face of the adapter body 115 of the connecting adapter 106. In addition, a second mounting concave portion 120 is provided in the back face of the adapter body 115 of the connecting adapter 106. The second mounting concave portion 120 of the connecting adapter 106 is formed in a concave shape so that either of a connector 100 (to be described later) of the electrical scalpel 16 and a connector 104 (to be described later) of the ultrasonic scalpel 102 can be selectively connected to the second mounting concave portion 120. A plurality of attracting parts 121 made of a magnetic material such as a permanent magnet are provided at the inside bottom of the second mounting concave portion 120 of the adapter body 115.

The electrical scalpel 16 is provided with a power supply on/off switch (not shown) for switching on and off the electrically driven section (not shown) provided in the inside of the electrical scalpel 16. In addition, the connector 100 connected to one end of the cable 17 of the electrical scalpel 16 is provided with two contacts 101a and 101b, a plurality of attracted parts 123, and one opening 124. The two contacts 101a and 101b are respectively arranged at positions corresponding to any two of the contact pins 116a to 116d of the connecting adapter 106, for example, the contact pins 116c and 116d. The plurality of attracted parts 123 are respectively arranged at positions corresponding to the attracting parts 121 of the connecting adapter 106, and the opening 124 is arranged at a position corresponding to the manipulating knob 117a of the mounting screw 117 of the connecting adapter 106.

The attracted parts 123 are made of a material such as a metal attractable to the magnetic material of the attracting parts 121 of the connecting adapter 106. The opening 124 of the connector 100 is formed to have a size and a depth which are large enough to allow the manipulating knob 117a of the mounting screw 117 of the connecting adapter 106 to be completely inserted into the opening 124.

The ultrasonic scalpel 102 is provided with a power supply on/off switch (not shown) for switching on and off the electrically driven section (not shown). One end of an electric cable 103 for supplying electrical power and control signals to the electrically driven section is integrally connected to the proximal end of the ultrasonic scalpel 102. The connector 104 is integrally provided at the other end of the electric cable 103. This connector 104 is provided with two contacts 105a and 105b, a plurality of attracted parts 123, and one opening 124. The two contacts 105a and 105b are respectively arranged at positions corresponding to any two of the contact pins 116a to 116d of the connecting adapter 106, for example, the contact pins 116a and 116b. The plurality of attracted parts 123 are respectively arranged at positions corresponding to the attracting parts 121 of the connecting adapter 106, and the opening 124 is arranged at a position corresponding to the manipulating knob 117a of the mounting screw 117 of the connecting adapter 106.

Either of the connector 100 of the electrical scalpel 16 and the connector 104 of the ultrasonic scalpel 102 can be selectively removably connected to the second mounting concave portion 120 of the connecting adapter 106. Incidentally, the details of the connector 104 are representatively shown in FIGS. 8 and 9.

The function of the third example will be described below. When the operation system is to be used, first of all, the operator covers the operation microscope 1 with the sterilizable sterilization drape 114 in such a manner as to cover the whole of the microscope body 3 and a part of the arm section 4. Then, the operator rotates the manipulating knob 117a of the mounting screw 117 while inserting the first mounting concave portion 119 of the connecting adapter 106 into the connecting portion 107 of the microscope body 3.

At this time, the respective point portions of the screw portion 118 and the contact pins 116a to 116d of the mounting screw 117 pierce through the sterilization drape 114. The respective contact pins 116a to 116d are then fitted into the contacts 108a to 108d of the external-device connecting portion 107 of the microscope body 3, whereby the respective contact pins 116a to 116d are electrically connected to the contacts 108a to 108d. When the operator further rotates the manipulating knob 117a of the mounting screw 117 to screw the screw portion 118 of the mounting screw 117 into the screw hole 113, the first mounting concave portion 119 of the connecting adapter 106 is fixed in the state of being fitted on the external-device connecting portion 107 of the microscope body 3.

Then, during this state, the operator connects an operation device to the second mounting concave portion 120 of the connecting adapter 106. When the ultrasonic scalpel 102 is to be used, the operator inserts the connector 104 into the second mounting concave portion 120 of the connecting adapter 106. During the process of inserting the connector 104, the attracted parts 123 of the connector 104 are attracted to the attracting parts 121 by the magnetic force of the attracting parts 121 of the connecting adapter 106, whereby the connecting adapter 106 and the connector 104 are fixed to each other. At the same time, contact is established between the contact pin 116a and the contact 105a and between the contact pin 116b and the contact 105b, whereby electrical connection is established between the contact pin 116a and the contact 105a and between the contact pin 116b and the contact 105b.

Furthermore, during the process of inserting the connector 104, at the same time, the manipulating knob 117a of the mounting screw 117 is inserted into the opening 124 of the connector 104. In this manner, the mounting screw 117 becomes unable to be manipulated from the outside.

During this state, the operator holds the ultrasonic scalpel 102 by hand and guides the ultrasonic scalpel 102 toward the site of operation of the patient H while observing the tip of the ultrasonic scalpel 102 under observation with the operation microscope 1.

After that, the operator manipulates the power supply on/off switch (not shown), whereby electrical power is supplied to the electrically driven section (not shown) in the inside of the ultrasonic scalpel 102 via the input means 110 to activate the ultrasonic scalpel 102. During this state, the operator performs a medical act such as treatment of the site of operation of the patient H. Incidentally, the operator can also set the electrical power to be supplied to the ultrasonic scalpel 102 to a desired output level by manipulating the input means 110 of the microscope body 3. In addition, since the control means 112 is connected to the ultrasonic scalpel 102 via the input means 110, the operator can also perform setting on control signals to be supplied to the ultrasonic scalpel 102, by manipulating the input means 110. For example, the operator can set, by manipulating the control means 112, electrical power for driving an ultrasonic vibrator (not shown) provided at the tip of the electrical scalpel 16 and a control signal to be supplied to the ultrasonic vibrator in order to change the frequency of ultrasonic vibration to be outputted from the ultrasonic vibrator, respectively, to desired output levels.

When the operator is to change the observing direction of the operation microscope 1, the operator changes the position of the microscope body 3 of the operation microscope 1. In the case where the operator temporarily stops using the ultrasonic scalpel 102, the operator holds the connector 104 of the ultrasonic scalpel 102, and pulls the connector 104 with a force larger than the attractive force between the attracting parts 121 and the attracted parts 123 of the connector 104. Accordingly, after the connector 104 has been removed from the connecting adapter 106, the operator performs the process of changing the position of the microscope body 3 of the operation microscope 1 and operation processes under observation with the operation microscope 1.

When the electrical scalpel 16 is to be used as an operation device, the operator inserts the connector 100 into the second mounting concave portion 120 of the connecting adapter 106 similarly to the case of the ultrasonic scalpel 102. At this time, the attracting parts 121 of the connecting adapter 106 and the attracted parts 123 of the connector 100 are attracted to one another, whereby the connector 100 is fixed to the second mounting concave portion 120 of the connecting adapter 106.

In the process of connecting the connector 100, contact is established between the contact pins 101a and 101b of the connector 100 and any ones of the contact pins 116a to 116d of the connecting adapter 106; for example, contact is established between the contact pin 116c and the contact 101a and between the contact pin 116d and the contact 101b, whereby electrical connection is established between the contact pin 116c and the contact 101a and between the contact pin 116d and the contact 101b. During this state, the operator holds the electrical scalpel 16 by hand and guides the electrical scalpel 16 toward a desired position in the site of operation of the patient H under observation with the operation microscope 1.

After that, the operator manipulates the power supply on/off switch (not shown), whereby electrical power is supplied to the electrically driven section (not shown) in the inside of the electrical scalpel 16. In addition, when the control means 112 is turned on, control signals for controlling the electrically driven section are supplied to the electrically driven section. In response to the electrical power and the control signals, the electrical scalpel 16 is appropriately activated. During this state, the operator performs an operation process such as treatment of the site of operation of the patient H. Incidentally, the operator can also set the electrical power and/or the control signals to be supplied to the electrical scalpel 16 to a desired output level by manipulating the input means 110 of the microscope body 3.

When the electrical scalpel 16 is to be removed from the connecting adapter 106, the operator needs only to pull the connector 100 in a direction in which to remove the connector 100 from the connecting adapter 106.

The third example serves the following advantages. Namely, in this example, the point portions of the respective contact pins 116a to 116d of the connecting adapter 106 have conical shapes so that the point portions can pierce and be inserted through the sterilization drape 114 made of a material such as vinyl. Accordingly, unlike the first example, it is not necessary to provide the mounting opening 15 for the connecting adapter 21 in the sterilization drape 14, and unlike the second example using the sterilization drape 59 having the connecting adapter 54, a dedicated sterilization is not needed and general sterilization drapes can be used. Accordingly, running costs can be reduced.

The two contacts 105a and 105b of the connector 104 of the ultrasonic scalpel 102 are provided at positions different from the positions where the two contacts 101a and 101b of the connector 100 of the electrical scalpel 16 are provided, and the respective contact pins 116a to 116d are provided in the connecting adapter 106 at positions corresponding to the contacts 101a, 101b, 105a and 105b. Accordingly, even if operation devices having different driving means are selectively connected to the second mounting concave portion 120 of the same connecting adapter 106, the operator does not fail to connect any of the operation devices and can easily connect and remove the operation devices.

Furthermore, the connecting adapter 106 is provided with the attracting parts 121 each made of a permanent magnet or the like and each of the connectors 100 and 104 is provided with the attracted parts 123, whereby the operator can carry out the process of selectively connecting and removing the connectors 100 and 104, through a simple process of selectively inserting and removing the connectors 100 and 104 into the second mounting concave portion 120 of the connecting adapter 106.

When each of the connectors 100 and 104 is mounted on the connecting adapter 106, the mounting screw 117 which connects the connecting adapter 106 to the microscope body 3 is fitted into the opening 124 of each of the connectors 100 and 104. Accordingly, there is no risk that when the operator is to remove the connector 100 or 104, the operator mistakenly removes the connecting adapter 106 and makes the vicinity of the microscope body 3 unclean.

Incidentally, in the third example, although the ultrasonic scalpel 102 and the electrical scalpel 16 are used as external devices, the kinds of external devices which constitute the operation system together with the operation microscope 1 are not limited to these devices, and may also include cauteries, ultrasonic probes and electronic endoscopes. In addition, the point portion of each of the contact pins 116a to 116d of the connecting adapter 106 and the point portion of the screw portion 118 of the mounting screw 117 have conical shapes so that the point portions can pierce and be inserted through the sterilization drape 114, but the point portions are not limited to such conical shapes and may assume any shape that can pierce and be inserted through the sterilization drape 114.

Although the examples of the invention have been described above, the invention is not limited to any of the above-described examples and can be embodied in various modified forms without departing from the scope of the invention.

The invention claimed is:

1. An operation system comprising:
    a sterilizable operation device having at least one of an observing section for observing a site of operation and an electrically driven section for treating the site of operation;
    an operation microscope having an observing optical system for enabling the site of operation to be observed at a magnified scale;
    a sterilization cover for covering at least a portion of the operation microscope, the sterilization cover being sterilizable;
    an electrically connecting portion provided in a microscope body of the operation microscope and constructed to supply at least one of an electrical power and an electrical signal to the operation device; and
    a connector interposed between the operation device and the electrically connecting portion, and having a contact portion capable of electrically connecting the operation device and the electrically connecting portion, the connector comprising:
    a first mounting portion disposed outside the sterilization cover and to which the operation device is removably connectable; and
    a second mounting portion disposed inside the sterilization cover and to which the electrically connecting portion of the operation microscope is removably connectable.

2. The operation system according to claim 1, wherein the sterilization cover is clamped between the operation microscope and the connector.

3. An operation system comprising:
    an electrically driven operation device for performing a medical act on a site of operation;
    an operation microscope enabling optical observation of the site of operation:
    an external-device connecting portion provided in the operation microscope and capable of supplying electrical power to the operation device;
    a sterilizable connecting adapter capable of being removably fixed to the external-device connection portion and of electrically connecting the operation microscope and the operation device
    a sterilization drape for retaining sterilization by covering at least a portion of the operation microscope; and
    clamping means provided on the connecting adapter for clamping the sterilization drape between the connecting adapter and the external-device connecting portion while retaining electrical connection between the connecting adapter and the external-device connecting portion as well as a sterilized state of the operation device.

4. An operation system according to claim 3 further comprising:
    a fixing part provided in the external-device connecting portion for fixing the sterilization drape and the connecting adapter to each other.

5. An operation system according to claim 3, wherein the connecting adapter is provided integrally with the sterilization drape.

6. An operation system comprising:
a sterilizable operation device having at least one electrically driven section for performing one of an observation and treatment on a site of operation;
an operation microscope having an observing optical system for enabling the site of operation to be observed at a magnified scale;
a sterilization cover for covering at least a portion of the operation microscope in a sterilized state;
at least one electrically connecting portion provided in a microscope body of the operation microscope and constructed to supply at least one of an electrical power and an electrical signal to the operation device;
a connector disposed between the operation device and the connecting portion and having a contact portion capable of electrically connecting the operation device and the connecting portion;
a first mounting portion provided in the and arranged outside the sterilization cover, the operation device being removably connectable to the first mounting portion; and
a second mounting portion provided in the connector and arranged inside the sterilization cover, the connecting portion being removably connectable to the second mounting portion.

7. An operation system according to claim 6, wherein the connector is made of a sterilizable material.

8. An operation system according to claim 6, wherein the connector has fixing means for fixing the sterilization cover around a periphery of the connecting portion.

9. An operation system according to claim 6, wherein the connector is integrally formed with the sterilization cover.

10. An operation system according to claim 6, wherein the second mounting portion and the first mounting portion have mutually different shapes.

11. An operation system according to claim 6, wherein the first mounting portion is adapted to accommodate multiple numbers of the operation devices.

12. The operation system according to claim 6, further comprising an input portion connected to the at least one electrically connecting portion for controlling at least one of the operation device and selecting functions of the operation device.

13. The operation system according to claim 6, wherein the sterilization cover is clamped between the operation microscope and the connector.

14. An adapter adapted to be interposed between an operation microscope and an external device in order to electrically connect the external device to the operation microscope, the adapter comprising:
at least one first mounting portion including a first electrode electrically connectable to the external device; and
a second mounting portion including a second electrode electrically connectable to an external-device connecting portion of the operation microscope,
wherein the adapter is removably connectable to both the operation microscope and the external device, the adapter has a fixing portion, the fixing portion having a sharp, point portion for piercing a sterilization cover and for preventing positional deviation of the sterilization cover by forming a hole in the sterilization cover when the adapter is mounted to the operation microscope, and the fixing portion comprises the second electrode.

15. An adapter adapted to be interposed between an operation microscope and an external device in order to electrically connect the external device to the operation microscope, the adapter comprising:
at least one first mounting portion including a first electrode electrically connectable to the external device;
a second mounting portion including a second electrode electrically connectable to an external-device connecting portion of the operation microscope; and
a sterilization cover integrally formed with the adapter wherein the adapter is removably connectable to both the operation microscope and the external device.

16. A method of electrically connecting an external device to an operation microscope having an external-device connecting portion, the method comprising:
connecting a first mounting portion of an electrical adapter to the external-device connecting portion of the operation microscope;
covering the operation microscope with a sterilization cover; and
connecting the external device to a second mounting portion of the electrical adapter.

* * * * *